(12) United States Patent
Ball et al.

(10) Patent No.: US 6,890,358 B2
(45) Date of Patent: May 10, 2005

(54) DISTAL COMPONENT FOR WRIST PROSTHESIS

(75) Inventors: Robert J. Ball, Winona Lake, IN (US); Ian A. Trail, Wigan (GB); Raphael Pascaud, Leeds (GB); Robert Beckenbaugh, Rochester, MN (US); William Geissler, Brandon, MS (US)

(73) Assignee: DePuy Products, Inc., Warsaw, IN (US)

( * ) Notice: Subject to any disclaimer, the term of this patent is extended or adjusted under 35 U.S.C. 154(b) by 0 days.

(21) Appl. No.: 10/396,644

(22) Filed: Mar. 25, 2003

(65) Prior Publication Data

US 2003/0216813 A1 Nov. 20, 2003

Related U.S. Application Data (60) Provisional application No. 60/368,740, filed on Mar. 29, 2002.

(51) Int. Cl.$^7$ .................................................. A61F 2/42
(52) U.S. Cl. ............................... 623/21.13; 623/21.14
(58) Field of Search .................. 623/21.11, 21.12, 623/21.13, 21.14, 21.15, 21.16, 21.17, 21.18, 21.19, 19.11–19.14, 20.34

(56) References Cited

U.S. PATENT DOCUMENTS

| | | | |
|---|---|---|---|
| 4,259,752 A | | 4/1981 | Taleisnik |
| 4,784,661 A | | 11/1988 | Beckenbaugh et al. |
| 5,019,103 A | * | 5/1991 | Van Zile et al. .......... 623/20.34 |
| 5,314,485 A | | 5/1994 | Judet |
| 5,458,646 A | | 10/1995 | Giachino et al. |
| 5,507,821 A | | 4/1996 | Sennwald et al. |
| 5,702,470 A | | 12/1997 | Menon |
| 5,766,258 A | | 6/1998 | Simmen |
| 5,782,926 A | | 7/1998 | Lamprecht |
| 5,954,722 A | | 9/1999 | Bono |
| 6,059,832 A | | 5/2000 | Menon |
| 6,086,614 A | | 7/2000 | Mumme |
| 6,168,630 B1 | | 1/2001 | Keller et al. |
| 6,224,634 B1 | | 5/2001 | Keller |
| 6,284,000 B1 | | 9/2001 | Ege |
| 6,485,520 B1 | | 11/2002 | Hubach et al. |
| 6,626,946 B1 | * | 9/2003 | Walch et al. ............ 623/19.11 |
| 2003/0114933 A1 | * | 6/2003 | Bouttens et al. ......... 623/19.13 |

FOREIGN PATENT DOCUMENTS

EP          1 066 807          1/2001

OTHER PUBLICATIONS

WO 01/47442, Bouttens et al, Jul. 5, 2001.*

* cited by examiner

*Primary Examiner*—Bruce E Snow
(74) *Attorney, Agent, or Firm*—Maginot, Moore & Beck (57) ABSTRACT

A distal component for a wrist prosthesis that utilizes fixation within the carpus complex, incorporates features that improve the probability of intercarpal fusion and allows modularity of articulating components. In one form, the subject invention includes an ovoid fixation plate having three holes and a boss. The three holes allow attachment of stems and/or screws distally for fixation in the carpus. The boss projects proximally from the plate, and serves as an attachment point for the articulating head. Modularity of the fixation and articulating components allow a surgeon many options for optimizing fixation distally, and articulation proximally. The proximal head of the distal component is designed to articulate with existing radial components. Since the proximal head of the distal component is modular, however, the head can be redesigned to accommodate later design changes in proximal components.

27 Claims, 9 Drawing Sheets

DISTAL COMPONENT FOR WRIST PROSTHESIS

This application claims the benefit of U.S. Provisional Application Ser. No. 60/368,740, filed Mar. 29, 2002.

TECHNICAL FIELD OF THE INVENTION

The present invention relates to wrist prostheses particularly for total wrist arthroplasty.

BACKGROUND OF THE INVENTION

A normal human wrist may be considered as comprising three sets of bones: the distal forearm, constituting the distal portion of the radius and the ulna; the carpals, constituting eight bones divided into two rows, i.e. the proximal bones (scaphoid, lunate, triquetrum, and pisiform) and the distal bones (trapezium, trapezoid, capitate, and hamate), that are most closely associated with the motion of the wrist; and the metacarpals, constituting the distal segments (i.e. thumb and four fingers).

The wrist is commonly considered a biaxial joint, meaning that there are two principle movements of the wrist, namely an extension-flexion movement and a radial/ulnar movement. Although the wrist has no intrinsic mechanism for active supination/pronation deviation movement, it is currently thought that there is likely some degree of passive motion associated with a torsional force transmitted across the radial-carpal joint. While various wrist prosthetics have been developed and patented, they all suffer from loosening of one of the two components of the wrist prosthetic. The torsional loads cannot be passed onto soft tissue due to the constrained design of prostheses. The torsional loads combined with media ulnar and radial deviation causing off center loads can lead to a "window-wiper" action of the central stem of the metacarpal component against the dorsal aspect of the middle metacarpal.

Recognition of such passive torsional forces has led to various wrist prosthetic designs that attempt to compensate for such passive torsional forces. These designs attempt to provide a more stable fixation. One type of stable fixation design that attempts to compensate for passive torsional forces adds rotational control pegs to a distal component of the wrist prosthetic. Another type of stable fixation design relies on screw-type fixation of a metacarpal component. Such designs have not been well received due to the inherently weak bone stock available for the metacarpal component in typical wrist implant patients. Also, some designs fail because there is an effort to obtain greater fixation, when motion is still present.

Another manner of attempting to compensate for such torsional forces is mismatching of wrist components. Particularly, a surgeon may match small metacarpal components with larger radial components. This, however, provides a less conforming articulating surface, thus allowing for greater contact stresses and greater potential for dislocation.

Another problem with wrist prosthetics is loosening of the distal implant component after implantation. In an attempt to solve this problem, various solutions have been proposed. These solutions, however, typically involve the creation of more and/or longer stems which are intended to penetrate deeper into the second, third, and fourth metacarpal canals. While at a first glance this solution seems probable to solve the problem. This solution, however, has not produced superior results to the primary implant outcome.

It would thus be advantageous to provide a distal component for a wrist prosthesis that overcomes one or more of the disadvantages of the prior art.

SUMMARY OF THE INVENTION

The subject invention is a distal component for a wrist prosthesis. Particularly, the subject invention is a distal component for a wrist prosthesis that utilizes fixation within the carpus complex, incorporates features that improve the probability of intercarpal fusion, and allows modularity of articulating components.

In one form, the subject invention provides a distal wrist component for a wrist prosthesis. The distal wrist component includes a fixation plate having a middle bore, two side bores, and a boss, a bushing disposed in the two side bores, and a head received on the boss. Each bushing is configured to receive a bone screw such that an end of the bone screw is flush with a surface of the fixation plate.

In another form, the subject invention provides a distal wrist component for a wrist prosthesis. The distal wrist prosthesis includes a fixation plate having first and second side bores and a middle bore with the first and second side bores having a spheric inner surface, a boss extending from a surface of the fixation plate and about the middle bore, a bushing disposed in the first and second side bores with each bushing having a spheric outer diameter matching the spheric inner surface of the first and second side bores such that the bushings are articulatable about the center of the spherical bore radius within the first and second side bores, and a head received on the boss.

In yet another form, the subject invention provides a distal wrist component for a wrist prosthesis. The distal wrist component includes a fixation plate having first and second peripheral bores and a middle bore, a boss extending from a surface of the fixation plate and about the middle bore, a bushing disposed in the first and second peripheral bores with each bushing having internal tapered threads adapted to receive a bone screw having an end with matching tapered thread such that when the bone screw is engaged in the bushing, the bushing is radially loaded to lock a trajectory of the bone screw at moments consistent with an amount of friction between the bushing and the fixation plate, and a head received on the boss.

In a particular form, the subject invention includes an ovoid fixation plate having three holes and a boss. The three holes allow attachment of stems and/or screws distally for fixation in the carpus. The boss projects proximally from the plate, and serves as an attachment point for the articulating head. Modularity of the fixation and articulating components allow a surgeon many options for optimizing fixation distally, and articulation proximally. The proximal head of the distal component is designed to articulate with existing radial components. Since the proximal head of the distal component is modular, however, the head can be redesigned to accommodate later design changes in radial components.

Particularly, the subject invention includes an ovoid-shaped base or fixation plate designed to accept attachment of two screws and a modular central stem. The two screws are peripherally attached to the ovoid-shaped fixation plate through the use of particularly designed bushings. The bushings allow the trajectory of the screws to be locked relative to the ovoid-shaped plate. The plate has two peripheral holes that are machined with an internal diameter that is preferably spherical in shape. The bushings have a matching spherical outer diameter is press fit into the plate such that the bushings may articulate within the hole of the plate. The bushing also contains internal threads that are tapered in diameter from largest at the proximal end of the bushing and smallest at the distal end. These threads accept a screw that has matching tapered threads such that when the screw is firmly engaged into the bushing, the bushing is radially loaded. This radial load(ing) locks the trajectory of the screw at moments consistent with the amount of friction between the bushing and the plate.

The distal side of the plate has a central hole with a precisely machined Morse taper. This allows a central stem to be received in the taper, rigidly attached by means of a set screw positioned through the proximal side of the plate. The plate also includes a proximal boss positioned centrally with respect to the medial/lateral direction and offset slightly dorsally in the anterior/posterior direction. The outer diameter of this boss has a precisely machined Morse taper designed to firmly engage an articulating surface proximally, and a flat surface distally, that roughly simulates a football sliced along its long axis. The articulating surface is designed such that is mates with certain existing radial component articulating surfaces.

The attachment of the articulating head to the fixation plate can exist in two embodiments. In one embodiment, the hole and boss are precisely machined so that the mating surfaces of the head and plate firmly engage, and provide a solid construct in vivo. In a second embodiment, the hole and boss are precisely machine such that the distal surface of the head bottoms out on the proximal surface of the plate. In the condition where these surfaces mate, the hole and boss do not engage, allowing rotation about the axis of the hole of the articulating head. Further, the modularity of the articulation heads allows options for offset rotation centers, varying head heights, varying degrees of articular laxity, materials, and/or motion.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

While the invention is susceptible to various modifications and alternative forms, specific embodiments thereof have been shown by way of example in the drawings and will herein by described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

Figure 1:
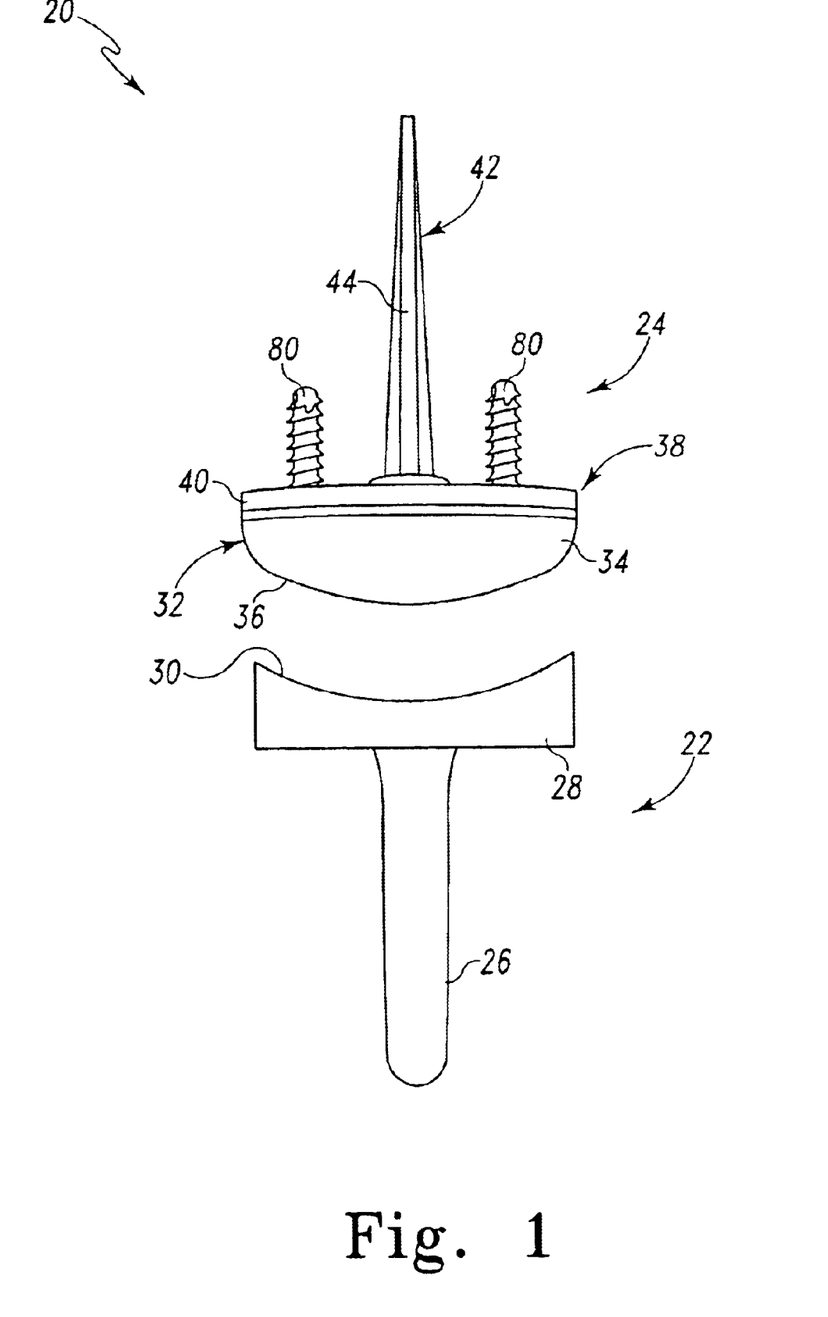
FIG. 1 is a partially exploded side view of an exemplary wrist prosthesis.

Referring now to FIG. 1 there is shown an exemplary embodiment of a wrist prosthesis in accordance with the principles of the subject invention, the wrist prosthesis generally designated 20. The wrist prosthesis 20 includes a radial or proximal component generally designated 22 and a carpal or distal component, generally designated 24. The proximal component 22 is configured, adapted and/or operative to be implanted into a radius of a patient. The distal component 24 is configured, adapted and/or operative to be implanted into carpals of the patient.

The proximal component 22 includes a stem 26 that is implanted into the radius of the patient. Situated on the stem 26 is a platform 28 that includes a curved or arcuate surface 30. The curved surface 30 provides a bearing surface for the distal component 24. Particularly, the curved surface 30 provides an articulation surface for the distal component 24 to articulate thereon. The proximal component 22 is manufactured from a material such as metal suitable for implantation, or various materials suitable for implantation with a plastic (e.g. polyethylene) insert (not shown) within the platform 28 to provide an articulating surface.

The distal component 24 includes a head, head portion, head component or the like generally designated 32, a fixation plate generally designated 38, and an anchor or stem generally designated 42. As explained below, the anchor 42 may constitute a stem as shown in FIG. 1 or may be a bone screw, or the other type of anchoring device. Shown in FIG. 1 and described hereinbelow, are two bone screws 80 that extend from the fixation plate 38. The bone screws 80 are configured to be anchored into the carpus of the patient. The head 32 may or may not be rotatable with respect to the fixation plate 38.

Figure 3:
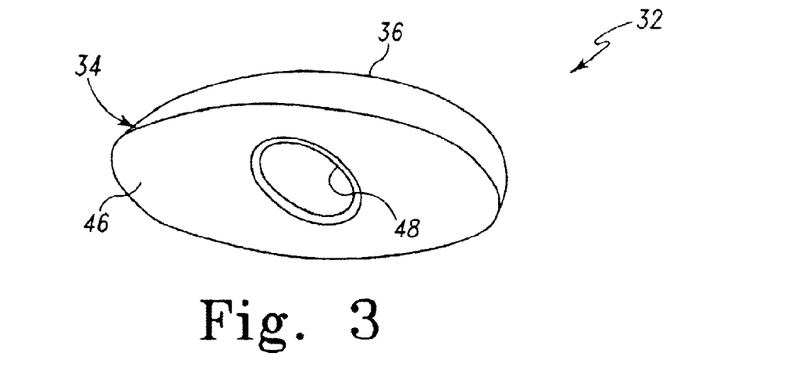
FIG. 3 is a bottom perspective view of an exemplary head of the exemplary distal wrist component of FIG. 2.
Figure 4:
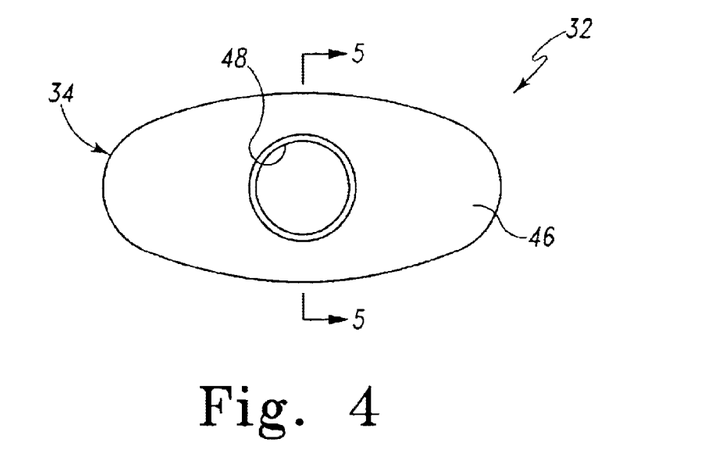
FIG. 4 is a bottom plan view of the exemplary head of FIG. 2.
Figure 5:
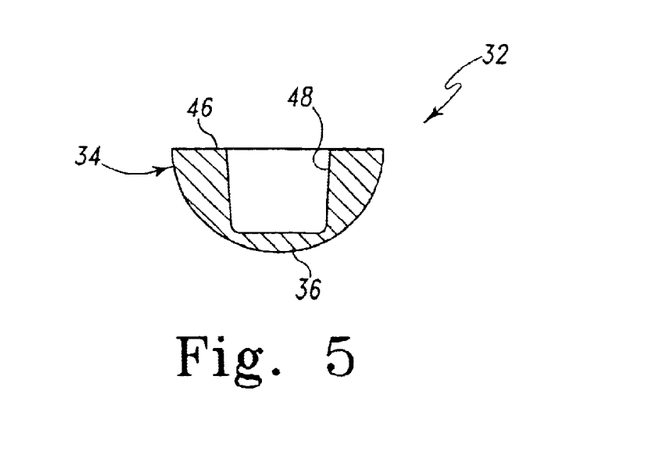
FIG. 5 is a sectional view of the exemplary head taken along line 5—5 of FIG. 4.

Referring to FIGS. 3–5, the head 32 is shown in greater detail. The head 32 is preferably made from a metal such as cobalt-chrome but other materials suitable for implantation and providing a bearing or articulation surface are acceptable. The head 32 is defined by a body 34 that is generally egg-shaped (ovoid or the like) cut along its longitudinal axis. As such, the body 34 defines an outer surface 36 that provides an arcuate or curved bearing surface. Preferably, the arcuate shape of the outer surface 36 matches the arcuate shape of the bearing surface 30 of the platform 28 of the proximal component 22. In this manner, the head 32 can essentially congruently bear against and articulate with respect to the proximal component 22.

The head 32 also has a bottom surface 46 that is preferably essentially flat. Since the head is ovoid-shaped, the bottom surface 46 essentially defines an ellipse. Disposed at the center of the bottom surface 46 is a recess, bore, hole, or the like 48. As discussed further below, the recess 48 is configured to receive or be received on a boss, protuberance, or the like.

Figure 6:
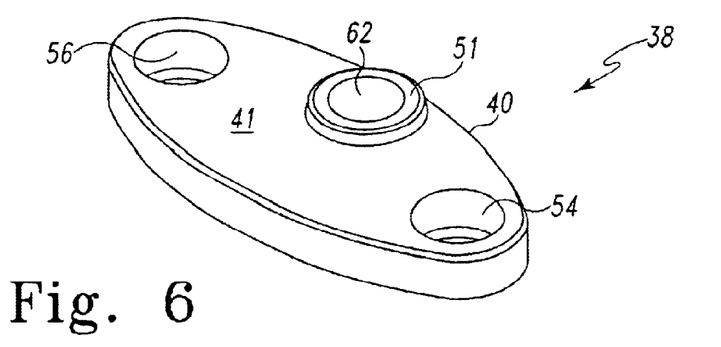
FIG. 6 is an enlarged perspective view of one side of an exemplary carpal fixation plate of the exemplary distal wrist component of FIG. 2.
Figure 7:
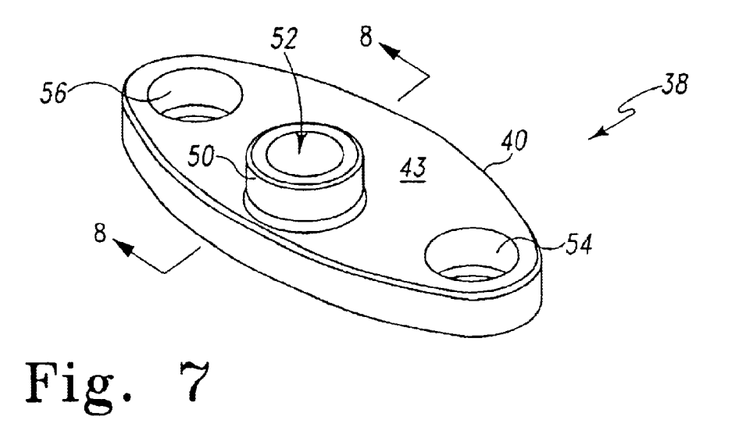
FIG. 7 is an enlarged perspective view of another side of an exemplary carpal fixation plate of the exemplary distal wrist component of FIG. 2.
Figure 8:
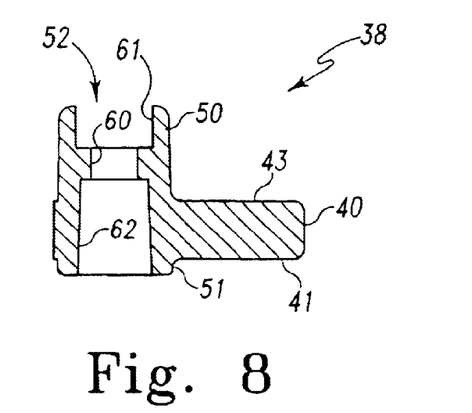
FIG. 8 is a sectional view of the exemplary carpal fixation plate taken along line 8—8 of FIG. 7.

Referring now to FIGS. 6–8, the exemplary fixation or mounting plate 38 is shown in greater detail. The fixation plate 38 is defined by a body 40 that is generally shaped as an ovoid, ellipse, or the like. The shape of the body 40 generally corresponds to the shape of the bottom 46 of the head 32. The body 40 has a bottom surface 41, a first hole 54 at one oblong end of the body 40 and a second hole 56 on another oblong end of the body 40. It should be appreciated that the terms first and second are arbitrary and thus may be interchanged without consequence. The body further includes a third hole 62 that may be slightly off center from a center point of the body 40. A small height rim 51 extends about the hole 62 from the bottom surface 41.

As seen in FIG. 7, the body 40 has a top surface 43 through which the holes 54 and 56 extend. Extending from the top surface 43 around hole 52 is a large height rim 50. The rim 50 defines a boss that is configured, adapted, and/or operative to receive the recess 48 of the head 32. The rim 50 may be configured to allow the surface 46 of the head 32 to touch the surface 43 of the fixation plate 38 or may be configured to allow the surface 46 of the head 32 to be immediately adjacent but not touching the surface 43 of the fixation plate. Typically, when the surfaces 46 and 43 touch, the head 32 is rotatable with respect to the fixation plate 38, and when the surfaces 46 and 43 do not touch, the head 32 is not rotatable with respect to the fixation plate 38. This, however, may not be the case.

The holes 54 and 56 are adapted to receive bushings therein, the bushings of which are described below. The bore 52 is adapted to receive the stem 42 and the set screw 96. Particularly, the bore 52 is defined by three diameter bores. More particularly, the bore 52 has a first diameter bore 61 opening onto the surface 43, a second diameter bore 62 opening onto the surface 41, and a third diameter bore 60 connecting the first and second diameter bores 61 and 62. The third diameter bore 60 is smaller than the first and second diameter bores 61 and 62. In one form, the second diameter bore 62 is slightly tapered. This is to receive the tapered end 90 of the stem body 44 when a stem is used as the center anchor. The first diameter is shown as a constant diameter bore. The bore 61 is sized to receive the head 100 of the set screw 96 or other like fastener if one is used (see FIGS. 14–15). The bore 60 is sized to allow the shank 98 of the set screw 96 to extend therethrough but not the head 100. The stem end 90 is received in the bore 62 while the shank 98 is threadedly received in the threaded bore 92 of the end 90 of the stem 42. It should be appreciated that other bore configurations may be utilized such as oppositely tapered bores that connect, a single one diameter bore, all depending on the main or center anchor and the manner in which the center anchor is affixed to the fixation plate 38.

The boss of the plate is positioned centrally with respect to the medial/lateral direction and offset slightly dorsally in the anterior/posterior direction. The outer diameter of this boss has a precisely machined Morse taper designed to firmly engage an articulating surface proximally, and a flat surface distally, that roughly simulates a football sliced along its long axis. The articulating surface is designed such that is mates with certain existing radial component articulating surfaces.

Figure 9:
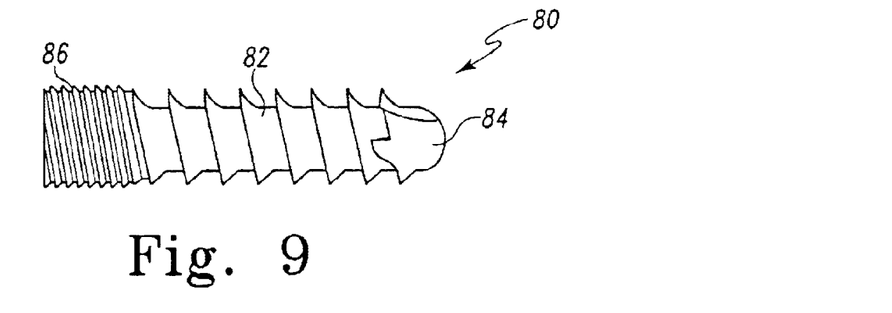
FIG. 9 is an enlarged plan view of an exemplary body screw of the exemplary distal wrist component of FIG. 2.

Referring to FIG. 9 the exemplary bone screw generally designated 80 is shown. The exemplary bone screw is utilized to fix the fixation plate 38 to the carpus of a hand. The bone screw 80 has a body 82 that has a plurality of radially expanded threads extending from a rounded tip 84 to an end 86. The end 86 is threaded with typical, smaller threads. The threads 86 may be straight or may be tapered depending on the configuration of the internal threads of the bushing (see below). An exemplary bone screw that may be used is described in further detail in U.S. Pat. No. 5,954,722 issued on Sep. 21, 1999 to Bono, entitled "Polyaxial Locking Plate" the specification of which is hereby incorporated by reference in its entirety.

Figure 10:
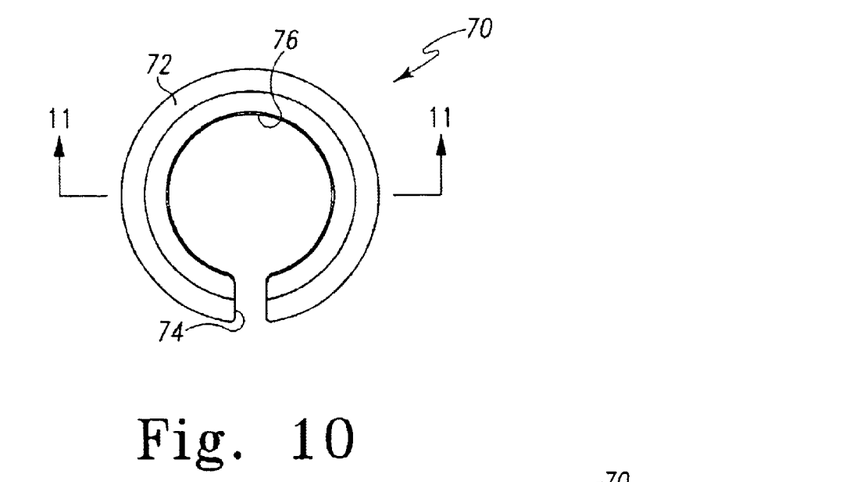
FIG. 10 is an enlarged plan view of an exemplary bushing of the exemplary distal wrist component of FIG.
Figure 11:
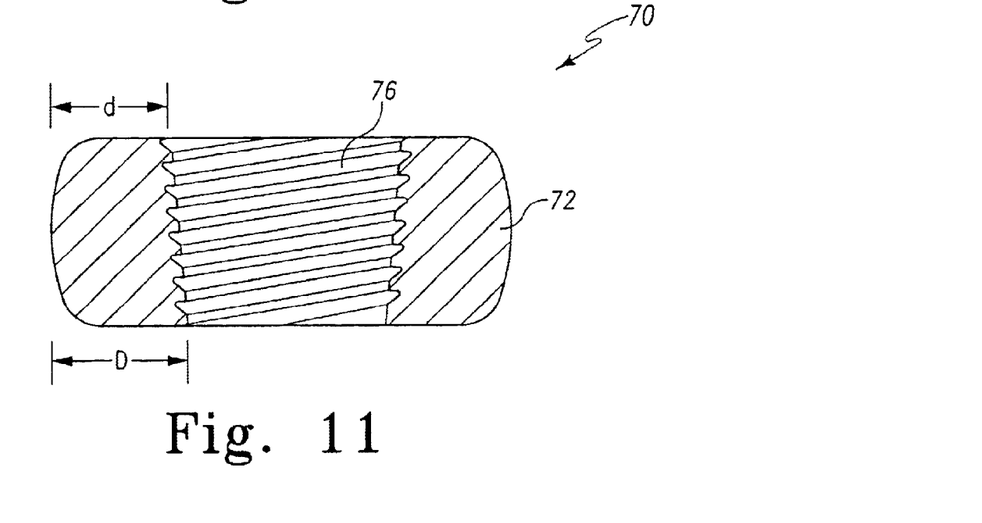
FIG. 11 is a sectional view of the exemplary bushing taken along line 11—11 of FIG. 10.

Referring to FIGS. 10 and 11 the exemplary bushing generally designated 70 is shown. The bushing 70 is defined by a generally annular or ring-shaped body 72 that includes a gap 74. The gap 74 allows the bushing to radially compress when inserted into the bores 54 and 56. This provides a press fit to retain the bushing 70 within the respective bore. The bushing 70 includes internal threads 76 that correspond to the threads of the end 86 of the bone screw 80. In one form, the threads 76 of the bushing 70 taper with respect to one end to the other end. This is illustrated by the distances d and D in FIG. 11. When d is smaller than D (i.e. d<D) there is a taper from the axial ends. When d equals D (i.e. d=D) there is no taper. It should be appreciated that the bone screw(s) 80, and particularly the threaded end 86 of the bone screw (s), interact with the bushing(s) 70. Various combinations of tapers and no tapers with respect to the bushing threads 76 and the bone screw end threads 86. The interaction of the bushing(s), the bone screw(s), and the fixation plate 38 will be described.

Figure 2:
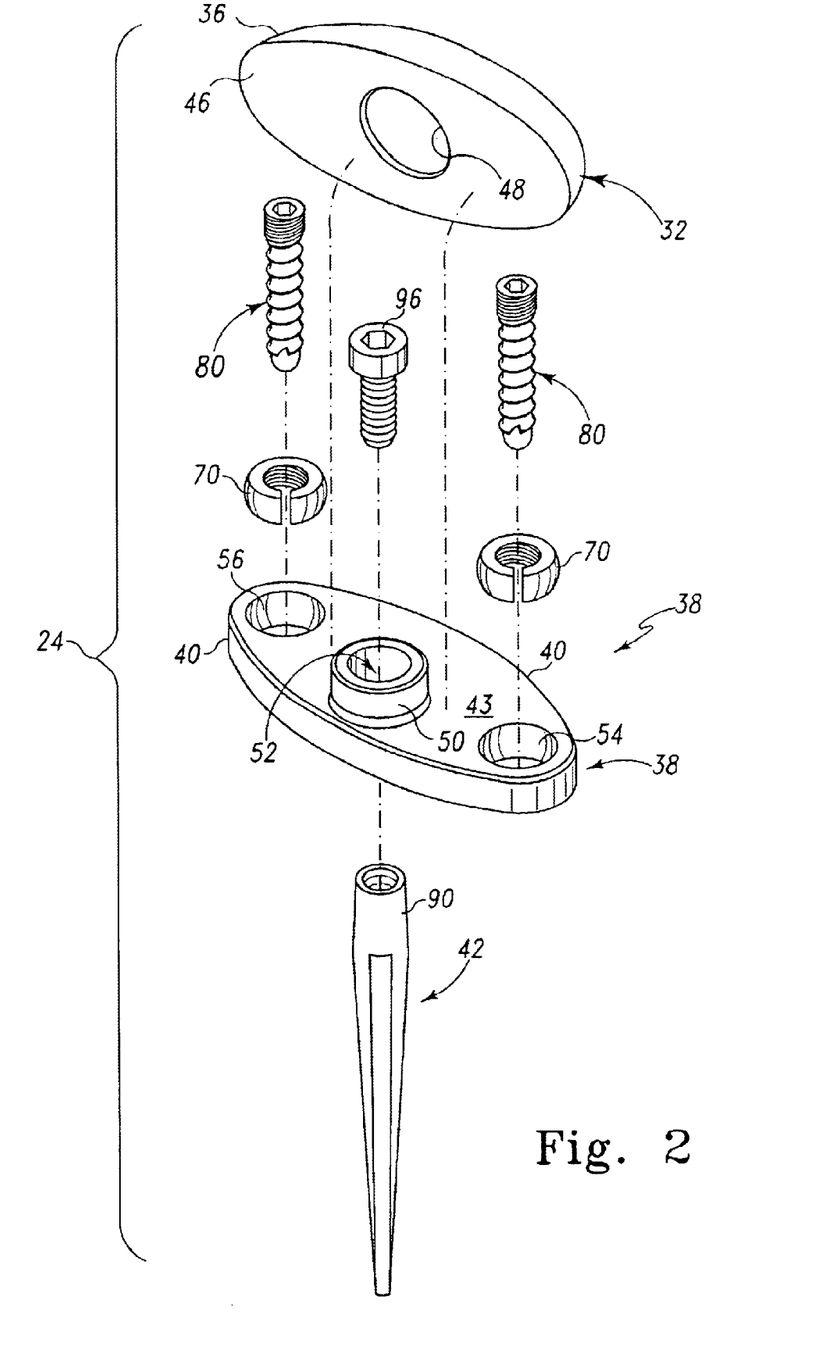
FIG. 2 is an exploded perspective view of an exemplary distal wrist component of the wrist prosthesis of FIG. 1.
Figure 16:
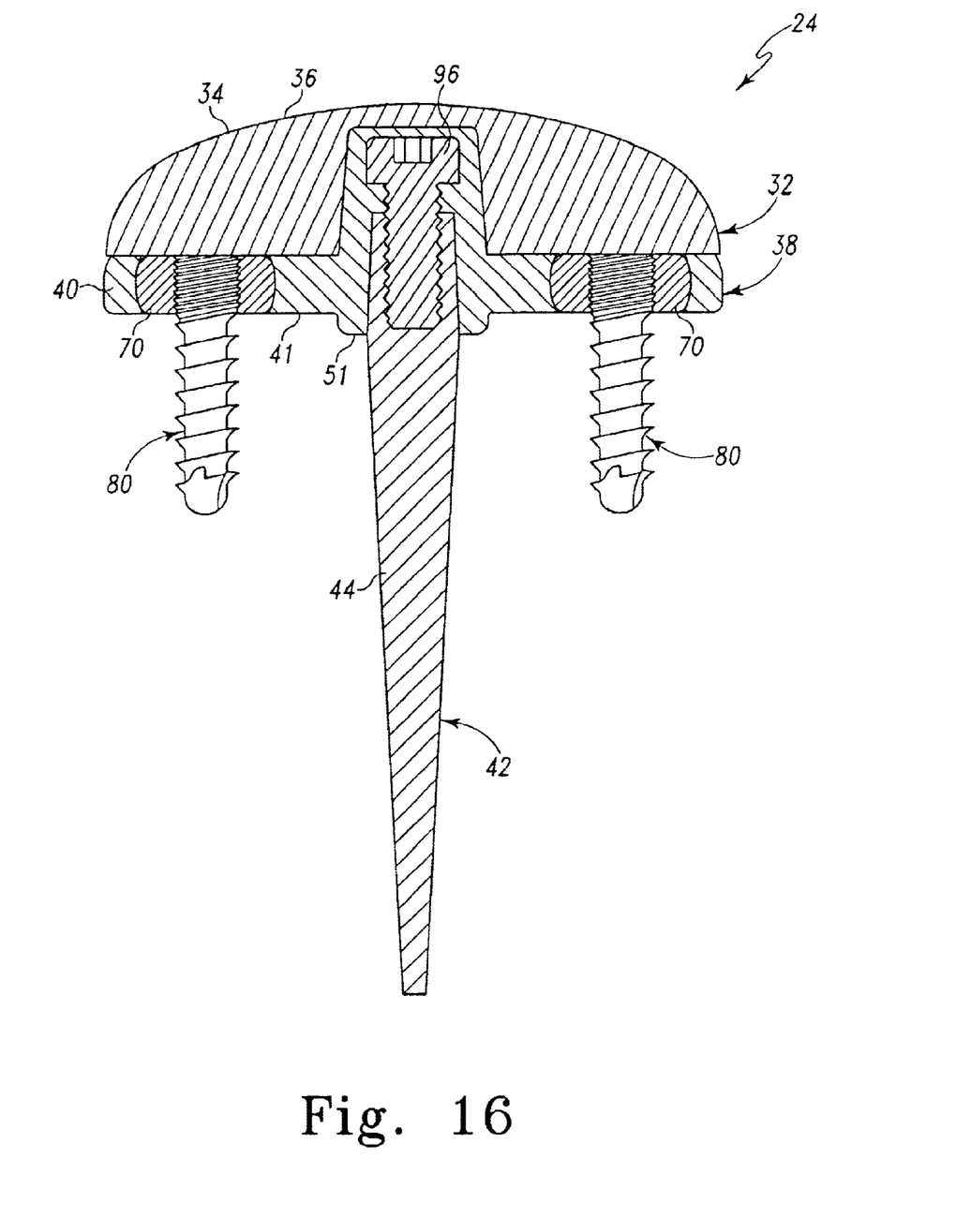
FIG. 16 is a sectional view of an assembled exemplary distal wrist component in accordance with the principles of the subject invention.

Particularly and with reference to FIGS. 2 and 16, the two bone screws 80 are peripherally attached to the fixation plate 38 through the use of the particularly designed bushings 70. The bushings 70 allow the trajectory of the bone screws 80 to be locked relative to the fixation plate 38. The two peripheral bores 54 and 56 of the fixation plate 38 are machined with an internal diameter that is preferably at least partially spherical in shape. The bushings 70 have a substantially mating spherical outer diameter (e.g. different radii) that is press fit into the bores 54 and 56 of the fixation plate 38 such that the bushings 70 may articulate within the bores 54 and 56 of the fixation plate 38. As indicated above, each bushing 70 also contains internal threads 76 that are preferably tapered in diameter from largest at a proximal end ("d") of the bushing and smallest at a distal end ("D"). These threads 76 accept the bone screw end 86 that has mating tapered threads such that when the bone screw 80 is firmly engaged into the bushing 70, the bushing 70 is radially loaded. This radial load(ing) locks the trajectory of the bone screw at moments consistent with the amount of friction between the bushing 70 and the fixation plate 38.

As described above, the bone screws 80 mate with the bushings 70. It should be appreciated that various combinations of threads, tapers, no tapers, and the like with respect to both the bone screws and the bushings can be made. Therefore, such combinations are contemplated and within the scope of the subject invention.

Figure 12:
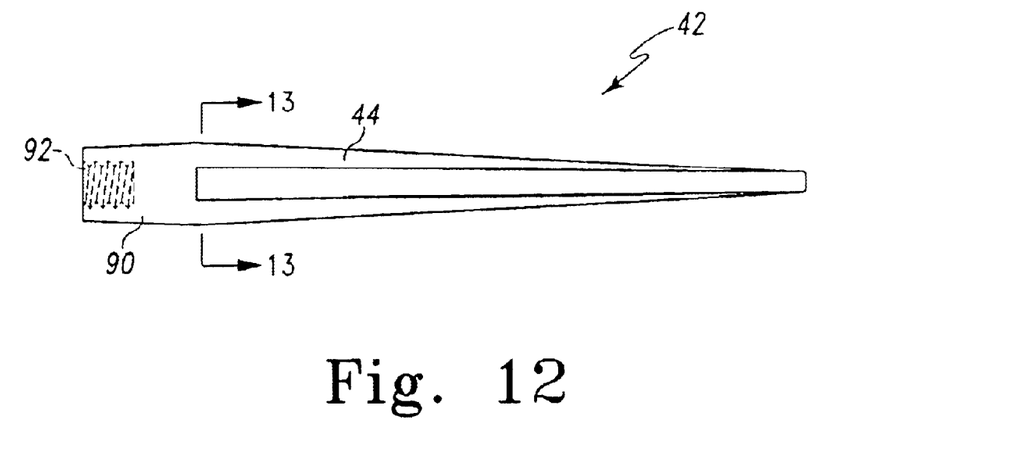
FIG. 12 is an enlarged plan view of an exemplary stem of the exemplary distal wrist component of FIG. 2.
Figure 13:
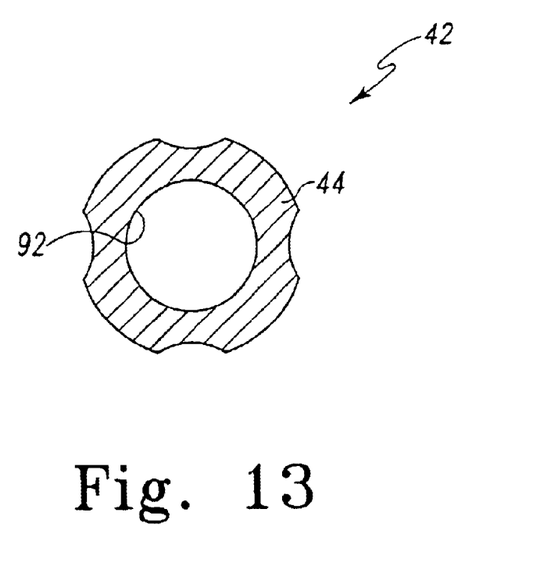
FIG. 13 is a sectional view of the exemplary stem taken along line 13—13 of FIG. 12.

Referring to FIGS. 12 and 13, the exemplary stem 42 is shown in greater detail. The stem 42 when used, functions as an anchor into the carpus, metacarpal and or bone of a finger. The stem is defined by a fluted and tapered body 44 that essentially forms a spike. The stem 44 has a neck 90 that may be tapered opposite to the taper of the body 44. A bore 92 that may be threaded as shown, is disposed at the end of the neck 90. The bore 92 is adapted to receive a pin (threaded or not depending on whether or not the bore 92 is threaded. As shown in FIG. 13, the tapered portion of the body 44 includes a hollow 94. It should be appreciated that more or less flutes than that shown may be provided on the stem. The stem flutes aid in anchoring the stem 44 against torsion.

Figure 14:
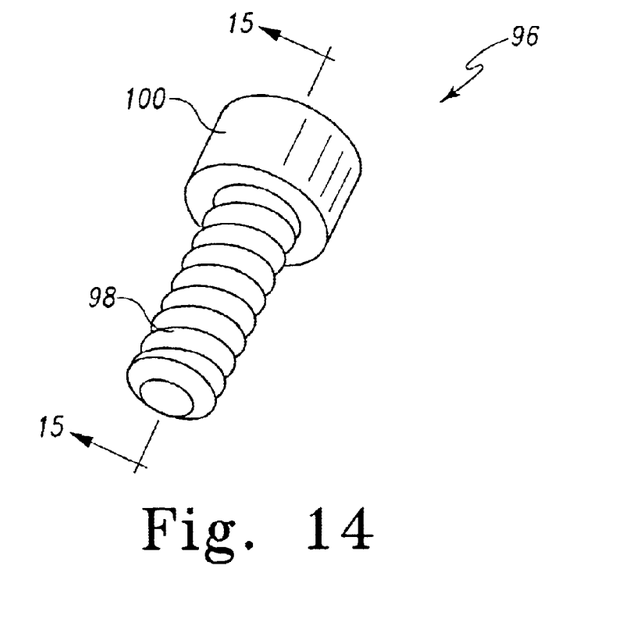
FIG. 14 is an enlarged plan view of an exemplary set screw of the exemplary distal wrist component of FIG. 2.
Figure 15:
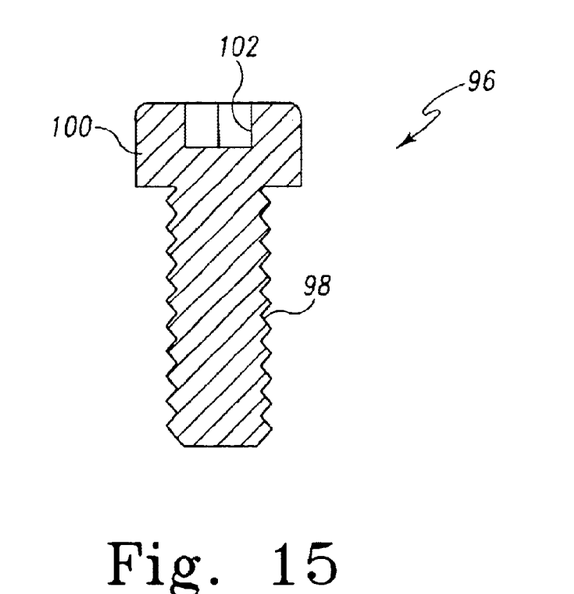
FIG. 15 is a sectional view of the exemplary set screw taken along line 15—15 of FIG. 14.

Referring now to FIGS. 14 and 15, the exemplary set screw 96 is shown in greater detail. The set screw 96 has a shank 98 that is threaded and a head 100. The head 100 includes a bore 102 that is configured to accept a driver for setting the set screw 96. The bore 102 may be configured as a hex, octagon, star, or the like. The threads of the shank 98 are complementary with the threads of the threaded bore 92 of the stem 42. While the set screw 96 is shown threaded, the set screw may not be threaded, depending on the type of fit or joining of the stem 42 and the fixation plate 38.

FIG. 2 depicts the distal component 24 in an exploded view to better illustrate the various constituent components thereof described above. It can be seen in FIG. 2 that the fixation plate 38 provides a base upon which the various components are or may be assembled. In particular, and during implantation, the stem 42 (central anchor) is inserted into the bore 52 of the fixation plate 38 from one side of thereof, particularly from the surface 41. The stem 42 may be affixed to the fixation plate 38 via the set screw 96 (or other fastener) that is inserted into the bore 52 from the other side (from surface 43) of the fixation plate 38.

A bushing 70 is press fit into each bore 54 and 56. Thereafter, a bone screw 80 is inserted through each bushing 70. As the tip 84 of each bone screw, then the shank 82 is received in a carpal (bone), the threaded end 86 is threadedly received by the threads 76 of the bushing 70. The bone screws are installed until the end of the end 86 is flush or below the surface 43. During this time, the fixation plate 38 is preferably held in place. Thereafter, the head 32 is placed onto the fixation plate 38. Particularly, the recess 48 of the head 32 is received onto the boss 50 either loosely or by a press fit. The entire construct constituting an exemplary distal component 24 in accordance with the principles of the subject invention is shown in cross-section in FIG. 16.

Figure 17:
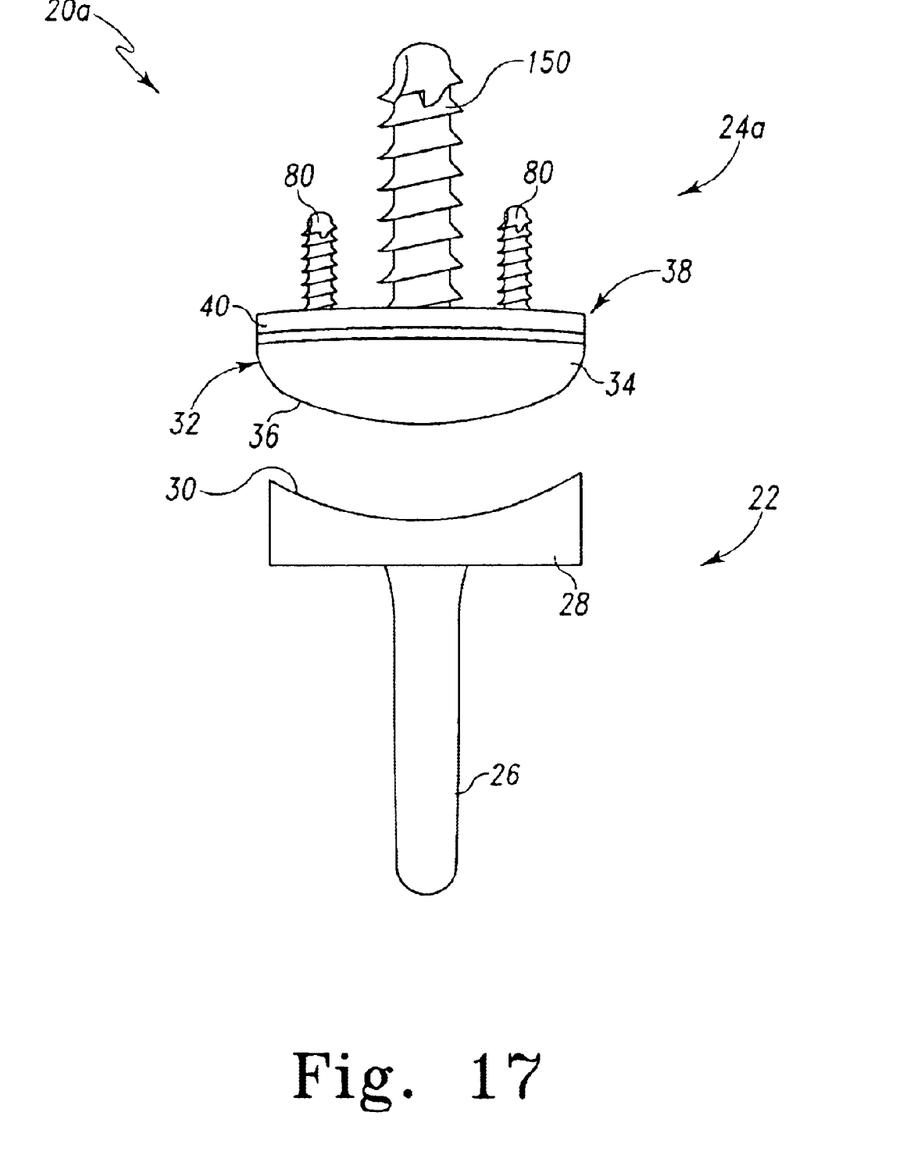
FIG. 17 is a front view of an alternative embodiment of a wrist prosthesis particularly having an alternative embodiment of a distal wrist component.

Referring now to FIG. 17, there is shown an alternative embodiment of a wrist prosthesis generally designated 20a. The wrist prosthesis includes a radial or proximal component generally designated 22 and a distal wrist component generally designated 24a. It should be appreciated that the components of the wrist prosthesis 20a and particularly the distal wrist component 24a that are different from the distal wrist component 24 are designated with an "a".

The distal wrist component 24a is generally the same as that described above with the exception of the central anchor. In this embodiment, the central anchor is a bone screw 150 here shown as larger than the bone screws 80. It should be appreciated, though, that the bone screw 150 may be the same size as the bone screws 80 or may be smaller. In the case of a central bone screw 150, the bore 52 (not seen in FIG. 17) of the fixation plate 38 would be adapted to receive the bone screw 150.

The above paragraph illustrates that the central anchor may be different depending on circumstances. In another example that is not shown herein, the distal wrist component does not have a central anchor. Of course, various combinations are contemplated.

The subject invention provides various features and/or advantages. For example, the subject distal wrist component provides a screw and bushing locking mechanism that provides a firmly positioned trajectory. This may lead to firmer carpal complex in the short term, thereby leading to higher probability of carpal fusion. As another example, the modular central stem attachment allows for varying shapes, lengths and/or sizes of central stems. As yet another example, the modular articulating head allows for varying shapes, heights, and/or forms of attachments. These can vary with patient indications and/or mating radial components. As still another example, the modular head allows the application of a mobile bearing concept in an embodiment where the hole in the head does not lock onto a boss on the plate. As a final example, the offset nature of the hole pattern in the plate more accurately matches anatomy, allows better placement of screw centers, and provides the potential of superior fusion performance.

There is thus a plurality of advantages of the subject invention arising from the various features of the wrist prosthesis described herein. It will be noted that alternative embodiments of the wrist prosthesis of the subject invention may not include all of the features described yet still benefit from at least some of the advantages of such features. Those of ordinary skill in the art may readily devise their own implementations of a wrist prosthesis that incorporate one or more of the features of the subject invention and fall within the sprit and scope of the subject invention.

What is claimed is:

1. A distal wrist component for a wrist prosthesis comprising:
    a fixation plate having a middle bore, two side bores, and a boss;
    a bushing disposed in said two side bores, each said bushing configured to receive a bone screw such that an end of the bone screw is flush with a surface of said fixation plate; and
    a head received on said boss,
    wherein said fixation plate is ovoid.

2. The distal wrist component of claim 1, wherein said boss is disposed about said middle bore.

3. The distal wrist component of claim 1, wherein said boss is positioned centrally with respect to a medial/lateral direction and offset slightly volarly in an anterior/posterior direction.

4. The distal wrist component of claim 1, wherein each said bushing has internal threads.

5. The distal wrist component of claim 4, wherein said internal threads of said bushing are tapered.

6. The distal wrist component of claim 5, wherein said internal threads are tapered from a larger diameter at a proximal end thereof to a smaller diameter at a distal end thereof.

7. The distal wrist component of claim 1, further comprising an anchor disposed in said middle bore.

8. A distal wrist component for a wrist prosthesis comprising:
    a fixation plate having first and second side bores and a middle bore, said first and second side bores having a spheric inner surface;
    a boss extending from a surface of said fixation plate and about said middle bore;
    a bushing disposed in said first and second side bores, each said bushing having a spheric outer diameter matching said spheric inner surface of said first and second side bores such that said bushings are articulateable within said first and second side bores; and
    a head received on said boss,
    wherein said fixation plate is ovoid.

9. The distal wrist component of claim 8, wherein said boss is positioned centrally with respect to a medial/lateral direction and offset slightly volarly in an anterior/posterior direction.

10. The distal wrist component of claim 8, wherein each said bushing has internal threads.

11. The distal wrist component of claim 10, wherein said internal threads of said bushing are tapered.

12. The distal wrist component of claim 11, wherein said internal threads are tapered from a larger diameter at a proximal end thereof to a smaller diameter at a distal end thereof.

13. The distal wrist component of claim 8, further comprising an anchor disposed in said middle bore.

14. A distal wrist component for a wrist prosthesis comprising:
- a fixation plate having first and second peripheral bores and a middle bore;
- a boss extending from a surface of said fixation plate and about said middle bore;
- a bushing disposed in said first and second peripheral bores, each said bushing having internal tapered threads adapted to receive a bone screw having an end with matching tapered thread such that when the bone screw is engaged in said bushing, said bushing is radially loaded to lock a trajectory of the bone screw at moments consistent with an amount of friction between said bushing and said fixation plate; and
- a head received on said boss,
wherein said fixation plate is ovoid.

15. The distal wrist component of claim 14, wherein said boss is positioned centrally with respect to a medial/lateral direction and offset slightly volarly in an anterior/posterior direction.

16. The distal wrist component of claim 14, wherein said internal threads of said bushings are tapered from a larger diameter at a proximal end thereof to a smaller diameter at a distal end thereof.

17. The distal wrist component of claim 14, further comprising an anchor disposed in said middle bore.

18. A wrist prosthesis, comprising:
- a support member having a first side bore, a second side bore, and a middle bore interposed therebetween, said support member further having a tapered boss;
- a first bushing positioned within said first side bore, said first bushing having a first set of internal threads that defines a first passageway;
- a first bone screw having a first externally threaded head that is configured to mate with said first set of internal threads of said first bushing;
- a second bushing located within said second side bore, said second bushing having a second set of internal threads that defines a second passageway;
- a second bone screw having a second externally threaded head that is configured to mate with said second set of internal threads of said second bushing;
- a head component having (i) a bearing surface, and (ii) a tapered recess configured to mate in a friction fit manner with said tapered boss of said support member.

19. The wrist prosthesis of claim 18, wherein said boss defines a passage that is aligned with said middle bore.

20. The wrist prosthesis of claim 19, further comprising:
- an anchor received within said middle bore of said support member, said anchor defining a threaded opening in a proximal part thereof, and
- a threaded fastener (i) received in said passage of said boss, and (ii) configured to threadingly engage said threaded opening of said proximal part of said anchor.

21. The wrist prosthesis of claim 20, wherein:
- said boss possesses an inwardly extending shoulder located within said passage,
- said fastener has a fastener head, and
- said shoulder is located between fastener head and said proximal part of said anchor when said fastener is threadingly engaged with said threaded opening of said proximal part of said anchor.

22. The wrist prosthesis of claim 21, wherein said fastener head is spaced apart from said head component.

23. A wrist prosthesis, comprising:
- a support member having a fastener bore and an anchor bore, said support member further having a tapered boss;
- a bushing positioned within said fastener bore, said bushing having a set of internal threads that defines a passageway;
- a bone fastener having a threaded head that is configured to mate with said set of internal threads of said bushing; and
- a head component having (i) a bearing surface, and (ii) a tapered recess configured to mate in a friction fat manner with said tapered boss of said support member.

24. The wrist prosthesis of claim 23, wherein said boss defines a passage that is aligned with said anchor bore.

25. The wrist prosthesis of claim 24, further comprising:
- an anchor received within said anchor bore of said support member, said anchor defining a threaded opening in a proximal part thereof, and
- a threaded fastener (i) received in said passage of said boss, and (ii) configured to threadingly engage said threaded opening of said proximal part of said anchor.

26. The wrist prosthesis of claim 25, wherein:
- said boss possesses an inwardly extending shoulder located within said passage,
- said fastener has a fastener head, and
- said shoulder is located between fastener head and said anchor when said fastener is threadingly engaged with said threaded opening of said proximal part of said anchor.

27. The wrist prosthesis of claim 26, wherein said fastener head is spaced apart from said head component.

* * * * *